United States Patent [19]

Furuya et al.

[11] Patent Number: 5,482,912

[45] Date of Patent: Jan. 9, 1996

[54] THERMOSENSITIVE RECORDING MATERIAL AND PHTHALIC ACID DERIVATIVES FOR USE IN THE SAME

[75] Inventors: Hiromi Furuya, Shimizu; Keishi Taniguchi, Susono; Hideo Suzaki, Numazu, all of Japan

[73] Assignee: Ricoh Company, Ltd., Tokyo, Japan

[21] Appl. No.: 201,993

[22] Filed: Feb. 25, 1994

[30] Foreign Application Priority Data

| Feb. 26, 1993 | [JP] | Japan | 5-062772 |
| May 24, 1993 | [JP] | Japan | 5-121745 |
| Jun. 17, 1993 | [JP] | Japan | 5-171160 |
| Dec. 14, 1993 | [JP] | Japan | 5-342419 |
| Feb. 21, 1994 | [JP] | Japan | 6-046439 |

[51] Int. Cl.$^6$ ............... B41M 5/26; B41M 5/40
[52] U.S. Cl. ............. 503/207; 503/216; 503/226
[58] Field of Search .................. 427/150, 151, 427/152; 503/200, 207, 216, 225, 226

[56] References Cited

U.S. PATENT DOCUMENTS

| 4,486,763 | 12/1984 | Taniguchi et al. | 503/209 |
| 4,502,068 | 2/1985 | Taniguchi et al. | 503/216 |
| 4,506,278 | 3/1985 | Sakamoto et al. | 503/216 |
| 4,511,910 | 4/1985 | Taniguchi et al. | 503/216 |
| 4,517,580 | 5/1985 | Iiyama et al. | 503/214 |
| 4,608,579 | 8/1986 | Taniguchi | 503/209 |
| 4,636,819 | 1/1987 | Nagamoto et al. | 503/216 |
| 4,731,354 | 3/1988 | Taniguchi et al. | 503/209 |
| 4,978,709 | 12/1990 | Taniguchi et al. | 524/606 |
| 4,983,446 | 1/1991 | Taniguchi et al. | 428/216 |
| 5,248,543 | 9/1993 | Yamaguchi et al. | 428/195 |
| 5,260,139 | 11/1993 | Shiraishi et al. | 428/488.1 |
| 5,296,439 | 3/1994 | Maruyama et al. | 503/201 |

FOREIGN PATENT DOCUMENTS 0190386  9/1985  Japan ................... 503/216

*Primary Examiner*—B. Hamilton Hess
*Attorney, Agent, or Firm*—Oblon, Spivak, McClelland, Maier & Neustadt

[57] ABSTRACT

A thermosensitive recording material composed of a support, and a thermosensitive recording layer formed on the support, containing a leuco dye and a color developer capable of inducing color formation in the leuco dye upon application of heat thereto, the color developer including at least one compound selected from the group consisting of the compounds of formulas (I) to (IV):

(Formula I):

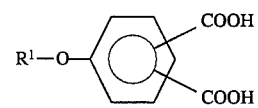

(Formula II):

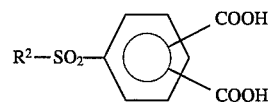

(Formula III):

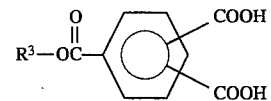

(Formula IV):

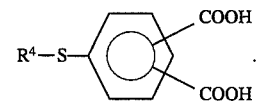

9 Claims, No Drawings

THERMOSENSITIVE RECORDING MATERIAL AND PHTHALIC ACID DERIVATIVES FOR USE IN THE SAME

BACKGROUND OF THE INVENTION

1. Field of the Invention

The present invention relates to a thermosensitive recording material, and more particularly to a thermosensitive recording material capable of producing images with excellent preservation stability, comprising as the main components a leuco dye serving as a coloring agent and a color developer capable of inducing color formation in the leuco dye upon application of heat thereto.

2. Discussion of Background

There are conventionally proposed various recording materials which utilize the coloring reaction between a colorless or light-colored electron donor type dye such as a leuco dye and a color developer capable of inducing color formation in the leuco dye upon application of heat or pressure thereto when brought into contact with the leuco dye.

A thermosensitive recording material, one of the above-mentioned recording materials, is proposed as disclosed in Japanese Patent Publications 43-4160 and 45-14039 and Japanese Laid-Open Patent Application 48-27736. Such a thermosensitive recording material is usable as a recording material for an electronic computer, facsimile apparatus, ticket vending apparatus, label printer, and recorder because it has the advantages that complicated processes such as development and image-fixing are not required, recording can be achieved for a short period of time using a relatively simple apparatus, there is no noise development, and the manufacturing cost is low.

In such a thermosensitive recording material, colorless or light-colored leuco dyes having a lactone, lactam, or a spiropyran ring are used as coloring dyes, and organic acids or phenols are conventionally employed as color developers. The thermosensitive recording material using the above-mentioned leuco dye and color developer is widely used for practical use because the produced images have high image density, with the whiteness of the background maintained high.

In line with the increase of a demand for the thermosensitive recording system, the requirements for improved preservability of the images recorded on the thermosensitive recording material with respect to the resistance to chemicals, light and heat are increased. Therefore, the development of a recording material capable of meeting the above-mentioned requirements is intensively desired.

To improve the preservation stability of the recorded images on the thermosensitive recording material, it is proposed to use as the color developer with high reliability a phenolsulfonic acid compound, as disclosed in Japanese Laid-Open Patent Applications 58-82788 and 60-13852; a metallic salt of benzoic acid, as disclosed in Japanese Laid-Open Patent Application 61-47292; and a substituted salicylic acid compound, as disclosed in Japanese Laid-Open Patent Application 62-169681. However, the fastness to fats and oils, plasaticizers, and water of the images recorded on the thermosensitive recording materials comprising the above-mentioned color developers is still insufficient.

The formation of an intermediate layer is proposed to increase the recording sensitivity of the thermosensitive recording material. For instance, there are proposed an intermediate layer mainly comprising a variety of inorganic pigments, and an intermediate layer comprising non-expandable void particles. However, these recording materials have the shortcomings that the thermal coloring sensitivity is insufficient and the recording properties are poor.

SUMMARY OF THE INVENTION

Accordingly, a first object of the present invention is to provide a thermosensitive recording material with high thermal coloring sensitivity and good recording properties, capable of coping with high-speed thermal recording, and producing images with improved resistances to fats and oils, and plasticizers to ensure the preservation stability.

A second object of the present invention is to provide a color developer for use in the thermosensitive recording material.

The above-mentioned first object of the present invention can be achieved by a thermosensitive recording material comprising a support and a thermosensitive recording layer formed on the support, comprising a leuco dye and a color developer capable of inducing color formation in the leuco dye upon application of heat thereto, the color developer comprising at least one compound selected from the group consisting of compounds represented by formulas (I) to (IV);

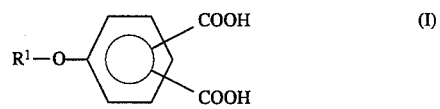

wherein $R^1$ is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group consisting of an alkyl group having 1 to 6 carbon atoms, an alkoxyl group having 1 to 6 carbon atoms, nitro group or a halogen,

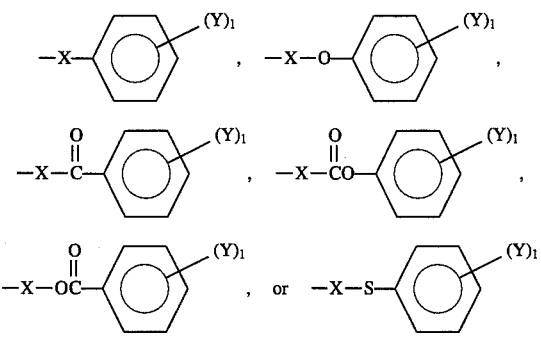

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and 1 is an integer of 0 to 5;

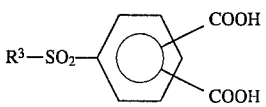 (II)

wherein R² is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group consisting of an alkyl group having 1 to 6 carbon atoms, an alkoxyl group having 1 to 6 carbon atoms, nitro group or a halogen,

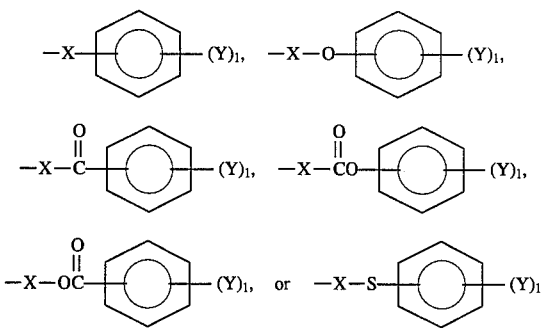

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and 1 is an integer of 0 to 5;

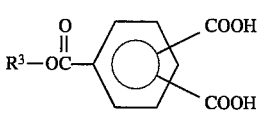 (III)

wherein R³ is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group consisting of an alkyl group having 1 to 6 carbon atoms, an alkoxyl group having 1 to 6 carbon atoms, nitro group or a halogen,

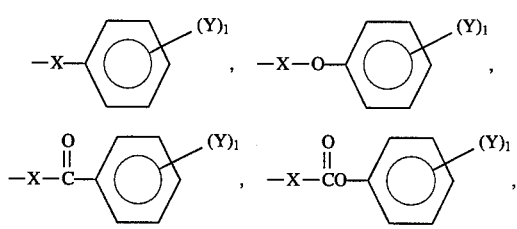

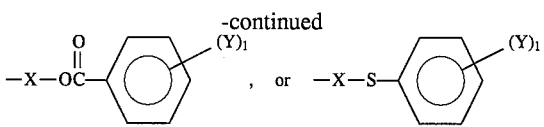

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and 1 is an integer of 0 to 5; and

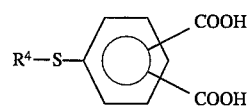 (IV)

wherein R⁴ is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group, consisting of an alkyl group having 1 to 6 carbon atoms, an alkoxyl group having 1 to 6 carbon atoms, nitro group or a halogen,

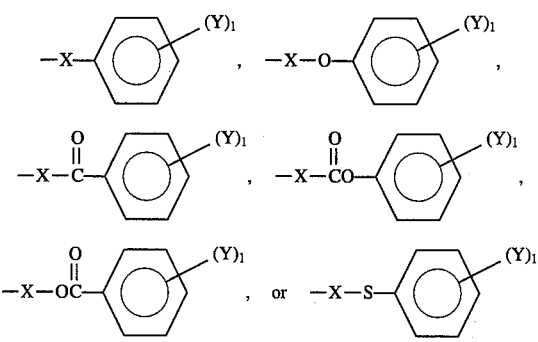

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and 1 is an integer of 0 to 5.

Furthermore, the first object of the present invention can also be achieved by a thermosensitive recording material comprising a support, an intermediate layer comprising spherical minute void particles comprising a thermoplastic resin, and a thermosensitive recording layer formed on the intermediate layer, comprising a leuco dye and a color developer capable of inducing color formation in the leuco dye upon application of heat thereto, the color developer comprising at least one compound selected from the group consisting of the above-mentioned compounds represented by formulas (I) to (IV).

In addition, the second object of the present invention can be achieved by novel phthalic acid derivatives of formulas (V) and (VI);

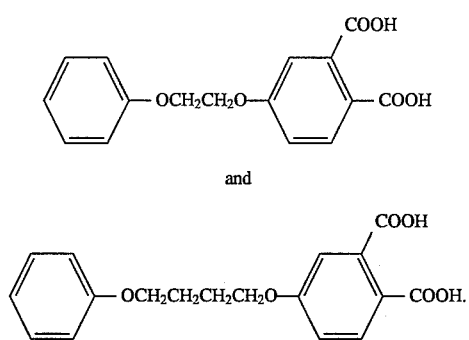

(V) and (VI)

DESCRIPTION OF THE PREFERRED EMBODIMENTS

The thermosensitive recording layer of the thermosensitive recording material according to the present invention comprises a color developer which comprises at least one compound selected from the group consisting of the above-mentioned compounds of formulas (I) to (IV), so that the preservation stability of the recorded images is improved, in particular, with respect to the resistances to fats and oils, and plasticizers.

The thermosensitive recording material of the present invention may further comprise an intermediate layer comprising as the main component plastic void particles in the form of sphere, which is provided between the support and the thermosensitive recording layer. The thermosensitivity of the recording material is improved owing to such an intermediate layer, so that the thermosensitive recording material becomes suitable for high-speed thermal recording.

In the present invention, the color developer for use in the thermosensitive recording layer comprises at least one compound selected from the group consisting of compounds of formulas (I) to (IV).

The chain hydrocarbon group in the definition of $R^1$ to $R^4$ in formulas (I) to (IV) have 1 to 10 carbon atoms, preferably 3 to 10 carbon atoms.

Specific examples of the compound of formula (I) are shown in Table 1:

TABLE 1

| Compound No. | Structural Formula |
|---|---|
| I-1 | Ph—CH₂O—C₆H₃(COOH)₂ |
| I-2 | Ph—CH₂CH₃O—C₆H₃(COOH)₂ |
| I-3 | Ph—OCH₃CH₂O—C₆H₃(COOH)₂ |
| I-4 | Ph—OCH₃CH(OH)—C₆H₃(COOH)₂ |
| I-5 | Ph—OC₂H₄OC₂H₄O—C₆H₃(COOH)₂ |
| I-6 | Ph—C(=O)CH₂CH₃O—C₆H₃(COOH)₂ |
| I-7 | Ph—CH(CH₃)O—C₆H₃(COOH)₂ |
| I-8 | Ph—CH(OH)CH₂CH₃O—C₆H₃(COOH)₂ |
| I-9 | (2-CH₃)C₆H₄—CH₂O—C₆H₃(COOH)₂ |
| I-10 | (4-Cl)C₆H₄—CH₃O—C₆H₃(COOH)₂ |
| I-11 | CH₃O—C₆H₄—OC₂H₄O—C₆H₃(COOH)₂ |
| I-12 | Ph—CH=CHCH₂O—C₆H₃(COOH)₂ |
| I-13 | Ph—OCH₂CH=CHCH₂O—C₆H₃(COOH)₂ |
| I-14 | Ph—OC₃H₆O—C₆H₃(COOH)₂ |
| I-15 | Ph—OC(=O)C₄H₈O—C₆H₃(COOH)₂ |
| I-16 | Ph—C(=O)OC₂H₄O—C₆H₃(COOH)₂ |
| I-17 | (3,5-(CH₃)₂)C₆H₃—OCH₂CH(OH)CH₂O—C₆H₃(COOH)₂ |

TABLE 1-continued

| Compound No. | Structural Formula |
|---|---|
| I-18 | Ph—OCH$_2$CHO—(C$_6$H$_3$)(COOH)$_2$, with CH$_2$OH substituent |
| I-19 | Ph—CH$_3$O—(C$_6$H$_3$)(COOH)$_2$ |
| I-20 | Ph—SCH$_2$CH$_2$O—(C$_6$H$_3$)(COOH)$_2$ |
| I-21 | Ph—SO$_2$CH$_2$CH$_2$O—(C$_6$H$_3$)(COOH)$_2$ |
| I-22 | Cl—C$_6$H$_4$—OC(=O)C$_4$H$_8$O—(C$_6$H$_3$)(COOH)$_2$ |
| I-23 | Ph—CH$_2$C(=O)CH$_2$O—(C$_6$H$_3$)(COOH)$_2$ |
| I-24 | Naphthyl—CH$_2$O—(C$_6$H$_3$)(COOH)$_2$ |
| I-25 | Ph—OCH$_2$CHCH$_2$O—(C$_6$H$_3$)(COOH)$_2$, with OH substituent |
| I-26 | HOCH$_2$CH$_2$O—(C$_6$H$_3$)(COOH)$_2$ |
| I-27 | (CH$_3$)$_3$CO—(C$_6$H$_3$)(COOH)$_2$ |
| I-28 | CH$_2$=CHOC$_2$H$_4$O—(C$_6$H$_3$)(COOH)$_2$ |
| I-29 | Ph—OCH$_3$CH$_2$CH$_2$CH$_3$O—(C$_6$H$_3$)(COOH)$_2$ |
| I-30 | Ph—CH$_2$OCH$_2$O—(C$_6$H$_3$)(COOH)$_2$ |
| I-31 | CH$_3$CH=CHCH$_2$O—(C$_6$H$_3$)(COOH)$_2$ |
| I-32 | (CH$_3$)$_2$CH—CH$_2$O—(C$_6$H$_3$)(COOH)$_2$ |
| I-33 | Naphthyl—CH$_2$O—(C$_6$H$_3$)(COOH)$_2$ |
| I-34 | Ph—O—CH$_2$O—(C$_6$H$_3$)(COOH)$_2$, with O substituent |
| I-35 | Cl—C$_6$H$_4$—OCH$_2$CH$_2$O—(C$_6$H$_3$)(COOH)$_2$ |
| I-36 | CH$_3$—C$_6$H$_4$—OCH$_2$CH$_2$O—(C$_6$H$_3$)(COOH)$_2$ |
| I-37 | Ph—SCH$_2$CH$_3$O—(C$_6$H$_3$)(COOH)$_2$ |
| I-38 | Ph—C(=O)CH$_2$CH$_2$CH$_2$O—(C$_6$H$_3$)(COOH)$_2$ |
| I-39 | Ph—CH$_2$C(=O)CH$_2$O—(C$_6$H$_3$)(COOH)$_2$ |
| I-40 | CH$_3$O—C$_6$H$_4$—OCH$_2$CHO—(C$_6$H$_3$)(COOH)$_2$, with CH$_3$ substituent |
| I-41 | (CH$_3$)$_2$—C$_6$H$_3$—OCH$_2$CH$_2$CH$_3$O—(C$_6$H$_3$)(COOH)$_2$ |

Specific examples of the compound of formula (II) are shown in Table 2:

TABLE 2

| Compound No. | Structural Formula |
|---|---|
| II-1 | C$_6$H$_5$—CH$_2$SO$_2$—C$_6$H$_3$(COOH)$_2$ |
| II-2 | CH$_3$—C$_6$H$_4$—CH$_2$SO$_3$—C$_6$H$_3$(COOH)$_2$ |
| II-3 | (2-CH$_3$)C$_6$H$_4$—CH$_3$SO$_2$—C$_6$H$_3$(COOH)$_2$ |
| II-4 | C$_6$H$_5$—CH$_2$CH$_2$SO$_2$—C$_6$H$_3$(COOH)$_2$ |
| II-5 | C$_6$H$_5$—CH(CH$_3$)SO$_2$—C$_6$H$_3$(COOH)$_2$ |
| II-6 | (2-Cl)C$_6$H$_4$—CH$_2$SO$_2$—C$_6$H$_3$(COOH)$_2$ |
| II-7 | NO$_2$—C$_6$H$_4$—CH$_2$SO$_3$—C$_6$H$_3$(COOH)$_2$ |
| II-8 | (CH$_3$)$_2$CHSO$_3$—C$_6$H$_3$(COOH)$_2$ |
| II-9 | (CH$_3$)$_2$C—SO$_3$—C$_6$H$_3$(COOH)$_2$ |
| II-10 | C$_2$H$_5$OC$_3$H$_4$SO$_2$—C$_6$H$_3$(COOH)$_2$ |
| II-11 | HOC$_2$H$_4$SO$_2$—C$_6$H$_3$(COOH)$_2$ |
| II-12 | CH$_2$=CHOC$_2$H$_4$SO$_2$—C$_6$H$_3$(COOH)$_2$ |
| II-13 | HOC$_2$H$_4$OC$_2$H$_4$SO$_2$—C$_6$H$_3$(COOH)$_2$ |
| II-14 | CH≡CCH$_3$SO$_2$—C$_6$H$_3$(COOH)$_2$ |
| II-15 | C$_6$H$_5$—C(=O)CH$_2$SO$_2$—C$_6$H$_3$(COOH)$_2$ |
| II-16 | CH$_3$—C$_6$H$_4$—C(=O)CH$_2$SO$_2$—C$_6$H$_3$(COOH)$_2$ |
| II-17 | C$_6$H$_5$—CH(OH)C$_3$H$_6$SO$_2$—C$_6$H$_3$(COOH)$_2$ |
| II-18 | C$_6$H$_5$—OC$_3$H$_6$SO$_2$—C$_6$H$_3$(COOH)$_2$ |
| II-19 | CH$_2$O—C$_6$H$_4$—OC$_6$H$_{10}$SO$_2$—C$_6$H$_3$(COOH)$_2$ |
| II-20 | NO$_2$—C$_6$H$_4$—OC$_2$H$_4$OC$_2$H$_4$SO$_2$—C$_6$H$_3$(COOH)$_2$ |
| II-21 | C$_6$H$_5$—OCH$_2$CH(OH)CH$_2$SO$_2$—C$_6$H$_3$(COOH)$_2$ |
| II-22 | CH$_3$—C$_6$H$_4$—OCH$_2$CH(CH$_2$OH)SO$_2$—C$_6$H$_3$(COOH)$_2$ |

TABLE 2-continued

| Compound No. | Structural Formula |
|---|---|
| II-23 | C₂H₆-〇-SC₃H₆SO₂-〇(COOH)(COOH) |
| II-24 | CH₃-〇(CH₃)-C(O)OC₄H₈SO₃-〇(COOH)(COOH) |
| II-25 | 〇-OC(O)C₂H₄SO₃-〇(COOH)(COOH) |
| II-26 | (naphthyl)-CH₂SO₂-〇(COOH)(COOH) |
| II-27 | CH₃-〇-CH₂SO₃-〇(COOH)(COOH) |
| II-28 | 〇-OCH₂CH₂SO₃-〇(COOH)(COOH) |
| II-29 | CH₃-〇(CH₃)-OCH₂CH(OH)CH₃SO₂-〇(COOH)(COOH) |
| II-30 | 〇-C(O)OC₄H₈SO₃-〇(COOH)(COOH) |
| II-31 | 〇-CH₂C(O)CH₂SO₃-〇(COOH)(COOH) |
| II-32 | 〇-CH₂CH₂SO₃-〇(COOH)(COOH) |
| II-33 | 〇-OCH₂CH₂SO₃-〇(COOH)(COOH) |

Specific examples of the compound of formula (III) are shown in Table 3:

TABLE 3

| Compound No. | Structural Formula |
|---|---|
| III-1 | 〇-CH₂OC(O)-〇(COOH)(COOH) |
| III-2 | 〇-CH₂CH₂OC(O)-〇(COOH)(COOH) |
| III-3 | 〇-OCH₂CH₂OC(O)-〇(COOH)(COOH) |
| III-4 | 〇-OCH₂CH(OH)OC(O)-〇(COOH)(COOH) |
| III-5 | CH₃-〇-CH₃OC(O)-〇(COOH)(COOH) |
| III-6 | 〇-CH(CH₃)OC(O)-〇(COOH)(COOH) |
| III-7 | Cl-〇-CH₃OC(O)-〇(COOH)(COOH) |
| III-8 | 〇-C(O)CH₃CH₂OC(O)-〇(COOH)(COOH) |
| III-9 | CH₃O-〇-OC₂H₄OC(O)-〇(COOH)(COOH) |
| III-10 | 〇-CH(OH)CH₂CH₂OC(O)-〇(COOH)(COOH) |
| III-11 | 〇-OC₂H₄OC₂H₄OC(O)-〇(COOH)(COOH) |
| III-12 | 〇-CH=CHCH₂OC(O)-〇(COOH)(COOH) |

TABLE 3-continued

| Compound No. | Structural Formula |
|---|---|
| III-13 | Ph—OCH$_2$CH=CHCH$_2$—C$_6$H$_3$(COOH)$_2$ |
| III-14 | Ph—OC$_3$H$_6$OC(=O)—C$_6$H$_3$(COOH)$_2$ |
| III-15 | Ph—OC(=O)C$_4$H$_8$OC(=O)—C$_6$H$_3$(COOH)$_2$ |
| III-16 | Ph—C(=O)OC$_2$H$_4$OC(=O)—C$_6$H$_3$(COOH)$_2$ |
| III-17 | (3,5-(CH$_3$)$_2$-C$_6$H$_3$)—OCH$_2$CH(OH)CH$_2$OC(=O)—C$_6$H$_3$(COOH)$_2$ |
| III-18 | Ph—OCH$_2$CH(CH$_2$OH)C(=O)—C$_6$H$_3$(COOH)$_2$ |
| III-19 | Ph—CH$_2$OC(=O)—C$_6$H$_3$(COOH)$_2$ |
| III-20 | Ph—SCH$_2$CH$_2$OC(=O)—C$_6$H$_3$(COOH)$_2$ |
| III-21 | Ph—SO$_2$CH$_2$CH$_2$OC(=O)—C$_6$H$_3$(COOH)$_2$ |
| III-22 | (4-Cl-C$_6$H$_4$)—OC(=O)C$_4$H$_8$OC(=O)—C$_6$H$_3$(COOH)$_2$ |
| III-23 | Ph—CH$_2$CC(=O)OC(=O)—C$_6$H$_3$(COOH)$_2$ |
| III-24 | (naphthyl)—CH$_3$OC(=O)—C$_6$H$_3$(COOH)$_2$ |

TABLE 3-continued

| Compound No. | Structural Formula |
|---|---|
| III-25 | Ph—OCH$_2$CH(OH)CH$_2$O—C$_6$H$_3$(COOH)$_2$ |
| III-26 | HOCH$_2$CH$_2$OC(=O)—C$_6$H$_3$(COOH)$_2$ |
| III-27 | (CH$_3$)$_3$C—OC(=O)—C$_6$H$_3$(COOH)$_2$ |
| III-28 | CH$_2$=CHOC$_2$H$_4$OC(=O)—C$_6$H$_3$(COOH)$_2$ |
| III-29 | Ph—OC$_3$H$_6$O—C(=O)—C$_6$H$_3$(COOH)$_2$ |

Specific examples of the compound of formula (IV) are shown in Table 4:

TABLE 4

| Compound No. | Structural Formula |
|---|---|
| IV-1 | Ph—CH$_2$S—C$_6$H$_3$(COOH)$_2$ |
| IV-2 | Ph—OC$_2$H$_4$S—C$_6$H$_3$(COOH)$_2$ |
| IV-3 | Ph—OC$_4$H$_8$S—C$_6$H$_3$(COOH)$_2$ |
| IV-4 | Ph—OCH$_2$C(CH$_3$)(CH$_2$)CH$_2$S—C$_6$H$_3$(COOH)$_2$ |
| IV-5 | (4-CH$_3$-C$_6$H$_4$)—OC$_3$H$_6$S—C$_6$H$_3$(COOH)$_2$ |
| IV-6 | Ph—CH$_2$CH$_2$S—C$_6$H$_3$(COOH)$_2$ |

TABLE 4-continued

| Compound No. | Structural Formula |
|---|---|
| IV-7 | Ph—OC₂H₄S—Ph(COOH)(COOH) |
| IV-8 | Ph—OC₄H₈S—Ph(COOH)(COOH) |
| IV-9 | Ph—C(O)CH₂CH₂S—Ph(COOH)(COOH) |
| IV-10 | CH₃—Ph—C(O)CH₂CH₂S—Ph(COOH)(COOH) |
| IV-11 | Cl—Ph—OCC₃H₆S—Ph(COOH)(COOH) |
| IV-12 | Ph(CH₃)—OCCH₃(CH₃)CH₂S—Ph(COOH)(COOH) |
| IV-13 | Ph—C(O)OC₂H₄S—Ph(COOH)(COOH) |
| IV-14 | Ph—SCH₂CH(CH₂OH)—Ph(COOH)(COOH) |
| IV-15 | Ph—SCH₂CHCH₃(OH)S—Ph(COOH)(COOH) |
| IV-16 | Cl—Ph(Cl)—SCH₂CH₃S—Ph(COOH)(COOH) |

In the case where the intermediate layer comprising as the main component plastic minute void particles is interposed between the support and the thermosensitive recording layer, the intermediate layer serves as a heat insulating layer, so that the thermal energy supplied by heat-application means such as a thermal head can be utilized efficiently to improve the thermosensitivity of the recording material.

The void particles for use in the intermediate layer comprise a thermoplastic resin for forming a shell of each void particle. A copolymer resin mainly comprising vinylidene chloride and acrylonitrile is preferably used as the above-mentioned thermoplastic resin. Air or other gasses are contained in the void particles in the expanded state.

It is preferable that the average particle diameter of the void particles be in the range from 2 to 10 μm in the present invention. When the particle size of the void particles is within the above range, there is no problem in the production of the intermediate layer because the voidage of the void particles can freely be determined. In addition, the surface smoothness of the intermediate layer is not decreased although it is prepared by coating a coating liquid comprising such void particles and drying the same, so that the adhesion of the recording layer to the thermal dead does not lower, and consequently, the thermosensitivity of the recording material can be prevented from deteriorating. When the above-mentioned advantages are further taken into consideration, it is preferable that the void particles classified in a narrow distribution be employed for use in the intermediate layer.

It is preferable that the voidage of the void particles for use in the intermediate layer be 50% or more, and more preferably 90% or more, from the viewpoint of the heat insulating effect. In the present invention, the voidage of the void particles for use in the intermediate layer is expressed by the following formula;

$$\text{Voidage (\%)} = \frac{\text{(inner diameter of void particles)}}{\text{(outer diameter of void particles)}} \times 100$$

When the voidage of the void particles is within the above range, sufficient heat insulating effect of the intermediate layer can be obtained, so that the thermal energy supplied by the thermal head is prevented from escaping through the support of the thermosensitive recording material. As a result, the thermosensitivity-improving effect can be increased. In the present invention, when the intermediate layer comprises void particles with an average particle diameter of 2 to 10 μm and a voidage of 90% or more, the flexibility of the obtained recording material is so much increased that the adhesion to the thermal head is further increased, thereby improving the dot reproduction performance.

The intermediate layer for use in the present invention may further comprise an inorganic or/and organic pigment. In this case, the oil absorption of the pigment is preferably 30 ml/100 g or more, and more preferably 80 ml/100 g or more.

The above-mentioned inorganic and/or organic pigment used in the intermediate layer, which may be employed alone or in combination, can be selected from any pigments for use in the conventional thermosensitive recording materials. Specific examples of the inorganic pigment are calcium carbonate, silica, zinc oxide, titanium oxide, aluminum hydroxide, zinc hydroxide, barium sulfate, clay, talc, and surface-treated calcium and silica. Specific examples of the organic pigment are urea-formaldehyde resin, styrene-methacrylic acid copolymer and polystyrene resin.

The thermosensitive recording layer of the recording material according to the present invention comprises a leuco dye serving as a coloring agent.

As the leuco dye for use in the present invention, which may be employed alone or in combination, any conventional dyes for use in the conventional leuco-dye-containing recording materials can be employed. For example, triphenylmethanephthalide leuco compounds, triallylmethane leuco compounds, fluoran leuco compounds, phenothiazine leuco compounds, thiofluoran leuco compounds, xanthene leuco compounds, indophthalyl leuco compounds, spiropyran leuco compounds, azaphthalide leuco compounds, couromeno-pyrazole leuco compounds, methine leuco compounds, rhodamineanilinolactam leuco compounds, rhodaminelactam leuco compounds, quinazoline leuco compounds, diazaxanthene leuco compounds and bislactone leuco compounds are preferably employed. Specific examples of those leuco dyes are as follows:

3,3-bis(p-dimethylanilino)phthalide,
3,3-bis(p-dimethylanilino)-6-dimethylaminophthalide (or Crystal Violet Lactone),
3,3-bis(p-dimethylanilino)-6-diethylaminophthalide,
3,3-bis(p-dimethylanilino)-6-chlorophthalide,
3,3-bis(p-dibutylanilino)phthalide,
3-cyclohexylamino-6-chlorofluoran,
3-dimethylamino-5,7-dimethylfluoran,
3-diethylamino-7-chlorofluoran,
3-diethylamino-7-methylfluoran,
3-diethylamino-7,8-benzfluoran,
3-diethylamino-6-methyl-7-chlorofluoran,
3-(N-p-tolyl-N-ethylamino)-6-methyl-7-anilinofluoran,
3-pyrrolidino-6-methyl-7-anilinofluoran,
2-(m-trifluoromethylanilino)-6-diethylaminofluoran,
2-[3,6-bis(diethylamino)-9-(o-chloroanilino)xanthylbenzoic acid lactam],
3-diethylamino-6-methyl-7-(m-trichloromethylanilino)fluoran,
3-diethylamino-7-(o-chloroanilino)fluoran,
3-dibutylamino-7-(o-chloroanilino)fluoran,
3-diamylamino-6-methyl-7-anilinofluoran,
3-(N-methyl-N-amylamino)-6-methyl-7-anilinofluoran,
3-(N-methyl-N-isopropylamino)-6-methyl-7-anilinofluoran,
3-(N-methyl-N-cyclohexylamino)-6-methyl-7-anilinofluoran,
3-(N-ethyl-N-isopropylamino)-6-methyl-7-anilinofluoran,
3-(N-methyl-N-isoamylamino)-6-methyl-7-anilinofluoran,
3-(N-methyl-N-isobutylamino)-6-methyl-7-anilinofluoran,
3-diethylamino-6-chloro-7-anilinofluoran,
3-(N-ethyl-N-2-ethoxypropylamino)-6-methyl-7-anilinofluoran,
3-(N-ethyl-N-tetrafurfurylamino)-6-methyl-7-anilinofluoran,
3-(N-ethyl-N-tetrahydrofurfurylamino)-6-methyl-7-anilinofluoran,
3-diethylamino-6-methyl-7-anilinofluoran,
3-dibutylamino-6-methyl-7-anilinofluoran,
3-diethylamino-5-methyl-7-(N,N-dibenzylamino)-fluoran,
benzoyl leuco methylene blue,
6'-chloro-8'-methoxy-benzoindolino-spiropyran,
6'-bromo-8'-methoxy-benzoindolino-spiropyran,
3-(2'-hydroxy-4'-dimethylanilino)-3-(2'-methoxy-5'-chlorophenyl)phthalide,
3-(2'-hydroxy-4'-dimethylanilino)-3-(2'-methoxy-5'-nitrophenyl)phthalide,
3-(2'-hydroxy-4'-diethylanilino)-3-(2'-methoxy-5'-tolyl)phthalide,
3-diethylamino-6-methyl-7-(2',4'-dimethylanilino)-fluoran,
3-(2'-methoxy-4'-dimethylanilino)-3-(2'-hydroxy-4'-chloro-5'-tolyl)phthalide,
3-morphorino-7-(N-propyl-trifluoromethylanilino)-fluoran,
3-pyrrolidino-7-trifluoromethylanilinofluoran,
3-diethylamino-5-chloro-7-(N-benzyl-trifluoromethylanilino)fluoran
3-pyrrolidino-7-(di-p-chlorophenyl)methylaminofluoran,
3-diethylamino-5-chloro-7-(α-phenylethylamino)-fluoran,
3-(N-ethyl-p-toluidino)-7-(α-phenylethylamino)-fluoran,
3-diethylamino-7-(o-methoxycarbonylphenylamino)-fluoran,
3-diethylamino-5-methyl-7-(α-phenylethylamino)-fluoran,
3-diethylamino-7-piperidinofluoran,
2-chloro-3-(N-methyltoluidino)-7-(p-N-butylanilino)-fluoran,
3-(N-ethyl-N-cyclohexylamino)-5,6-benzo-7-α-naphtylamino-4'-bromofluoran,
3-(N-benzyl-N-cyclohexylamino)-5,6-benzo-7-α-naphthylamino-4'-bromofluoran,
3-diethylamino-6-methyl-7-mesidino-4',5'-benzofluoran,
3-(p-dimethylanilino)-3-[1,1-bis(p-dimethylanilino)-ethylene-2-yl]phthalide,
3-(p-dimethylanilino)-3-[1,1-bis(p-dimethylanilino)-ethylene-2-yl]-6-dimethylaminophthalide,
3-(p-dimethylanilino)-3-(1-p-dimethylanilino-1-phenylethylene-2-yl)phthalide,
3-(p-dimethylanilino)-3-(1-p-dimethylanilino-1-p-chlorophenylethylene-2-yl)-6-dimethylaminophthalide,
3-(4'-dimethylamino-2'-methoxy)-3-(1"-p-dimethylanilino-1"-p-chlorophenyl-1",3"-butadiene-4"-yl)benzophthalide,
3-(4'-dimethylamino-2'-benzyloxy)-3-(1"-p-dimethylanilino-1"-phenyl-1",3"-butadiene-4"-yl)-benzophthalide,
3,6-bis(dimethylamino)fluorenespiro(9,3')-6'-dimethylaminophthalide,
3-dimethylamino-6-dimethylamino-fluorene-9-spiro-3'-(6'-dimethylamino)phthalide,
3,3-bis-[2-(p-dimethylanilino)-2-(p-methoxyphenyl)-ethenyl]-4,5,6,7-tetrachlorophthalide,
3-bis[1,1-bis(4-pyrrolidinophenyl)ethylene-2-yl]-5,6-dichloro-4,7-dibromophthalide,
bis(p-dimethylaminostyryl)-1-naphthalenesulfonylmethane, and
bis(p-dimethylaminostyryl)-1-p-tolylsulfonylmethane.

In the thermosensitive recording material according to the present invention, the color developer comprises at least one compound selected from the group consisting of the previously mentioned compounds of formulas (I) to (IV). Furthermore, when necessary, other electron-acceptors, for instance, phenolic compounds, thiophenolic compounds, thiourea derivatives, organic acids and metallic salts thereof can be employed in combination with the compounds (I) to (IV). Specific examples of such electron-acceptors are as follows:

4,4'-isopropylidenebisphenol,
4,4'-isopropylidenebis(o-cresol),
4,4'-sec-butylidenebisphenol,
4,4'-isopropylidenebis(o-tert-butylphenol),
4,4'-cyclohexylidenebisphenol,
4,4'-isopropylidenebis(2-chlorophenol),
2,2'-methylenebis(4-methyl-6-tert-butylphenol),
2,2'-methylenebis(4-ethyl-6-tert-butylphenol),
4,4'-sec-butylidenebis(6-tert-butyl-2-methylphenol),
1,1,3-tris(2-methyl-4-hydroxy-5-cyclohexylphenyl)butane,
4,4'-thiobis(6-tert-butyl-2-methylphenol),
2,4'-diphenolsulfone,
2,2'-diallyl-4,4'-dihydroxydiphenylsulfone,
3,4'-dihydroxy-4'-methyldiphenylsulfone,
4-isopropoxy-4'-hydroxydiphenylsulfone,
4-benzyloxy-4'-hydroxydiphenylsulfone,
4,4'-diphenolsulfoxide,
isopropyl p-hydroxybenzoate,
benzyl p-hydroxybenzoate,
benzyl protocatechuate,
stearyl gallate,
lauryl gallate,
octyl gallate,
1,7-bis(4-hydroxyphenylthio)-3,5-dioxaheptane,
1,5-bis(4-hydroxyphenylthio)-3-oxapentane,
1,3-bis(4-hydroxyphenylthio)-propane,
monocalcium salt of monobenzyl phthalate,
N,N'-diphenylthiourea, N,N'-di(m-chlorophenyl)thiourea,
salicylanilide,
antipyrine complex of zinc thiocyanate,
zinc salt of 1-acetyloxy-2-naphthoic acid,
zinc salt of 2-acetyloxy-3-naphthoic acid,
zinc salt of 2-acetyloxy-1-naphthoic acid,
bis(4-hydroxyphenyl)methyl acetate,
bis(4-hydroxyphenyl)benzyl acetate,
4-[β-(p-methoxyphenoxy)ethoxy]salicylic acid,
1,3-bis(4-hydroxyphenyl)benzene,
1,4-bis(4-hydroxyphenyl)benzene,
4,4'-diphenolsulfone,
3,3'-diallyl-4,4'-diphenolsulfone,
α,α-bis(4-hydroxyphenyl)-α-methyltoluene,
tetrabromobisphenol A,
tetrabromobisphenol S,
4,4'-thiobis(2-methylphenol),
4,4'-thiobis(2-chlorophenol),
zinc p-nitrobenzoate,
1,3,5-tris(4-tert-butyl-3-hydroxy-2,6-dimethylbenzyl)isocyanuric acid,
2,2-bis(3,4'-dihydroxyphenyl)propane, and
bis(4-hydroxy-3-methylphenyl)sulfide.

To obtain a thermosensitive recording material according to the present invention, a variety of conventional binder agents can be employed in the thermosensitive recording layer for binding the above-mentioned leuco dyes, color developers, and auxiliary components to be described later to the support of the thermosensitive recording material. Alternatively, when the intermediate layer is provided between the support and the thermosensitive recording layer, the plastic minute void particles may be bound and supported on the support. As the binder agent used to prepare the thermosensitive recording layer and the intermediate layer, any conventional binder agents used in the conventional thermosensitive recording materials can appropriately be employed.

Examples of the binder agent are water-soluble polymers such as polyvinyl alcohol, starch and starch derivatives, cellulose derivatives such as methoxy cellulose, hydroxyethyl cellulose, carboxymethyl cellulose, methyl cellulose and ethyl cellulose, sodium polyacrylate, polyvinyl pyrrolidone, acrylamide-acrylic ester copolymer, acrylamide-acrylic ester-methacrylic acid terpolymer, alkali salts of styrene-maleic anhydride copolymer, alkali salts of isobutylene-maleic anhydride copolymer, polyacrylamide, sodium alginate, gelatin, and casein; emulsions such as polyvinyl acetate, polyurethane, polyacrylic ester, polymethacrylic ester, vinyl chloride-vinyl acetate copolymer, and ethylene-vinyl acetate copolymer; and latexes such as styrene-butadiene copolymer and styrene-butadiene-acrylic copolymer.

In the present invention, the thermosensitive recording layer may comprise a thermofusible material as the thermosensitivity-improving agent.

The specific examples of the above-mentioned thermofusible material are as follows: fatty acids such as stearic acid, and behenic acid; fatty amides such as stearic acid amide, and palmitic acid amide; fatty acid metallic salts such as zinc stearate, aluminum stearate, calcium stearate, zinc palmitate, and zinc behenate; and p-benzylbiphenyl, terphenyl, triphenylmethane, benzyl p-benzyloxybenzoate, β-benzyloxy naphthalene, phenyl β-naphthoate, phenyl 1-hydroxy-2-naphthoate, methyl 1-hydroxy-2-naphthoate, diphenyl carbonate, guaiacol carbonate, dibenzyl terephthalate, dimethyl terephthalate, 1,4-dimethoxynaphthalene, 1,4-ethoxynaphthalene, 1,4-dibenzyloxynaphthalene, 1,2-bis(phenoxy)ethane, 1,2-bis(3-methylphenoxy)ethane, 1,2-bis(4-methylphenoxy)ethane, 1,4-bis(phenoxy)butane, 1,4-bis(phenoxy)-2-butene, 1,2-bis(4-methoxyphenylthio)ethane, dibenzoylmethane, 1,4-bis-(phenylthio)butane, 1,4-bis(phenylthio)-2-butene, 1,2-bis(4-methoxyphenylthio)ethane, 1,3-bis(2-vinyloxyethoxy)benzene, 1,4-bis(2-vinyloxyethoxy)benzene, p-(2-vinyloxyethoxy)biphenyl, p-aryloxybiphenyl, p-propargyloxybiphenyl, dibenzoyloxymethane, 1,3-dibenzoyloxypropane, dibenzyl disulfide, 1,1-diphenylethanol, 1,1-diphenylpropanol, p-(benzyloxy)benzylalcohol, 1,3-diphenoxy-2-propanol, N-octadecylcarbamoyl-p-methoxycarbonylbenzene, N-octadecylcarbamoylbenzene, dibenzyl oxalate, bis(4-methylbenzyl)oxalate, bis(4-chlorobenzyl)oxalate, 1,5-bis(p-methoxyphenyloxy)-3-oxapentane, and 1,2-bis(4-methoxyphenoxy)propane.

When necessary, the thermosensitive recording layer for use in the present invention may further comprise auxiliary additive components such as a filler, a surface active agent, a lubricant and an agent for preventing color formation by pressure application, which are used in the conventional thermosensitive recording materials.

Examples of the filler for use in the present invention are finely-divided particles of inorganic fillers such as calcium carbonate, silica, zinc oxide, titanium oxide, aluminum hydroxide, zinc hydroxide, barium sulfate, clay, kaolin, talc, surface-treated calcium and surface-treated silica; and finely-divided particles of organic fillers such as urea-formaldehyde resin, styrene-methacrylic acid copolymer, polystyrene resin and vinylidene chloride resin.

Examples of the lubricant for use in the present invention include higher fatty acids and amides, esters and metallic salts thereof; and a variety of waxes such as an animal wax, a vegetable wax, a mineral wax, and a petroleum wax.

The thermosensitive recording material of the present invention may further comprise an additional layer comprising a pigment, a binder agent and a thermofusible material when necessary, which is provided between the previously mentioned intermediate layer and the thermosensitive recording layer.

Furthermore, the thermosensitive recording material may further comprise a protective layer which is provided on the thermosensitive recording layer in order to improve the preservation stability of the recorded images and the writing quality of the recording material. The protective layer comprises the previously mentioned pigment, binder agent, and thermofusible material.

The color developer for use in the present invention comprises at least one compound selected from the group consisting of the previously mentioned compounds of formulas (I) to (IV) as shown in Tables 1 to 4. Among these compounds, the compound No. I-3 and the compound No. I-29 shown in Table 1 are novel compounds and superior in the color development performance. In addition, the preservation stability, particularly, the resistances to fats and oils, and plasticizers of both an image portion and a background portion of the recording material is improved by using these compounds No. I-3 and No. I-29 as the color developers in the thermosensitive recording material.

The method of synthesizing the compound of formula (I) will now be explained with reference to the synthesis of the compound No, I-3.

The compound No. I-3 can be prepared by the conventional reaction, for instance, in accordance with the following reaction scheme (1), (2) or (3):

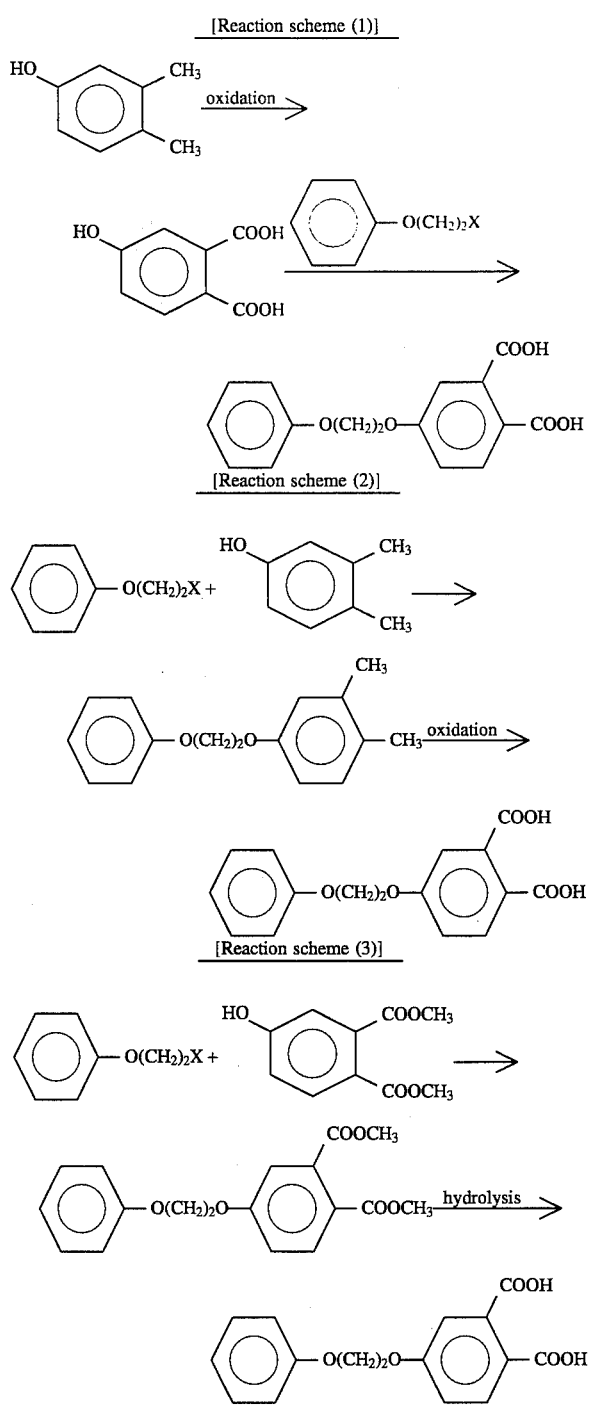

In the above-mentioned reaction schemes (1) to (3), X is a halogen atom. The previously mentioned compounds of formulas (II) and (IV) serving as the color developers in the present invention can also be synthesized in accordance with the reaction schemes similar to those as mentioned above. To synthesize the compound of formula (III), the reaction schemes (1) and (2) are applicable because the synthesis reaction including the process of hydrolysis is not preferable.

More specifically, the compound No. I-29 can be synthesized in the following manner: dimethyl 4-hydroxyphthalate is allowed to react with 4-halogeno-1-phenoxybutane in the presence of an alkali. The reaction product thus obtained is subjected to hydrolysis in the presence of an alkali, so that the compound No. I-29 can be prepared. In the above-mentioned reaction, potassium hydroxide and sodium hydroxide are preferably employed as the alkali compounds. As the halogen substituent of the above-mentioned phenoxybutane derivative, bromine and chlorine are preferably employed. Any solvents in which dimethyl 4-hydroxyphthalate and 4-halogeno-1-phenoxybutane can be dissolved and a small amount of an alkaline aqueous solution can be uniformly dissolved are preferable as the solvent for use in the above reaction. For instance, ethanol, methanol and dimethyl sulfoxide are preferably employed as the solvent. In this case, the use of a high boiling point solvent can curtail the reaction time. A solvent in which the materials cannot completely be dissolved may also be employed in such a condition that the materials are dispersed therein, or it may be used in combination with a good solvent. When necessary, a catalyst capable of transferring between an organic phase and a water phase, for example, quaternary ammonium salts such as triethylbenzylammonium chloride, tetramethylammonium chloride and tetramethylammonium bromide can be employed.

A substituted methyl phthalate obtained by the reaction is subjected to hydrolysis in the presence of an alkali, so that a desired compound can be obtained. The hydrolysis reaction may be carried out using a solvent in which both the substituted methyl phthalate and water are dissolved, or without any solvent. In the case where no solvent is employed, it is desirable to carry out the hydrolysis reaction in a large quantity of water containing sodium hydroxide or potassium hydroxide in an amount of about 5 to 10 wt. % at a temperature as high as about 100° C. In this case, it is preferable to use 3 moles or more of the alkali compound to 1 mole of the substituted methyl phthalate in the hydrolysis reaction.

In the case where the hydrolysis reaction proceeds in a large quantity of alkaline water without any solvent, the alkaline water becomes colorless and transparent when a half ester is obtained. It is preferable to heat the alkaline water after the alkaline water becomes transparent in order to complete the hydrolysis reaction. After the completion of the hydrolysis reaction, an acid such as hydrochloric acid or sulfuric acid which is appropriately diluted is added dropwise to the alkaline solution, so that a desired product separates out. The reaction mixture is dispersed for several hours with the pH of the reaction mixture maintained at about 3 while heating to about 60° to 70° C. Thus, the substitution is completed and the desired product separates out.

Then, the obtained product is purified when necessary. It is preferable to purify the product by the recrystallization from a solvent such as water, alcohol, toluene, ethyl acetate, hexane or a mixed solvent thereof.

Other features of this invention will become apparent in the course of the following description of exemplary embodiments, which are given for illustration of the invention and are not intended to be limiting thereof.

SYNTHESIS EXAMPLE 1

6.5 (0.1 mol) g of potassium hydroxide with a purity of 86% were dissolved in 100 ml of ethanol. Then, 21.1 g (0.1 mol) of dimethyl 4-hydroxyphthalate were dissolved in the above prepared solution. To the mixture thus obtained, 21.2 g (0.1 mol) of 4-bromo-1-phenoxybutane were added dropwise. After completion of the addition of 4-bromo-1-phenoxybutane, the reaction of the above prepared mixture was carried out over a period of about 4 hours under reflux of ethanol.

After the completion of the reaction, ethanol was distilled away from the reaction mixture by using a rotary evaporator, so that white solid separated out. The resulting white solid was isolated by filtration and washed with about 500 ml of tap water repeatedly, and then dried. Thus, 28.0 g (0.078 mol) of dimethyl 4-(4'-phenoxybutoxy)phthalate were obtained.

The thus obtained dimethyl 4-(4'-phenoxybutoxy)phthalate was subjected to hydrolysis over a period of 30 hours under reflux of water using 500 ml of tap water in which 16.4 g (0.25 mol) of potassium hydroxide with a purity of 86% were dissolved.

After cooling of the reaction mixture, the reaction mixture was adjusted to pH 3 by using hydrochloric acid, so that crystals separated out. The resulting crystals were recrystallized from ethyl acetate, so that 22.1 g of 4-(4'-phenoxybutoxy)phthalic acid were obtained. The melting point of this compound was 160° C.

The results of the NMR spectral analysis of the obtained product are shown in Table 5. The product was identified as 4-(4'-phenoxybutoxy)phthalic acid through the NMR analysis.

TABLE 5

| 4.088 ppm | (a, b) | 8H |
|---|---|---|
| 6.90–7.4 ppm | (c, d) | 7H |
| 7.722 ppm | (e) | 1H | structure: (d)(d)(d)(d)(d)–OCH₂CH₂CH₂CH₂O–(c)(e)(c)–COOH, COOH
(with labels (a)(b)(b)(a) on the OCH₂CH₂CH₂CH₂O chain)

SYNTHESIS EXAMPLE 2

6.5 g (0.1 mol) of potassium hydroxide with a purity of 86% were dissolved in 100 ml of ethanol. Then, 21.1 g (0.1 mol) of dimethyl 4-hydroxyphthalate were dissolved in the above prepared solution. To the mixture thus obtained, 20.1 g (0.1 mol) of β-bromo-1-phenetole were added dropwise. After completion of the addition of β-bromo-1-phenetole, the reaction of the above prepared mixture was carried out over a period of about 4 hours under reflux of ethanol.

After the completion of the reaction, ethanol was distilled away from the reaction mixture by using a rotary evaporator, so that white solid separated out. The resulting white solid was isolated by filtration and washed with about 500 ml of tap water repeatedly, and then dried. Thus, 26.8 g (0.081 mol) of dimethyl 4-(β-phenoxyethoxy)phthalate were obtained.

The thus obtained dimethyl 4-(β-phenoxyethoxy)phthalate was subjected to hydrolysis over a period of 30 hours under reflux of water using 500 ml of tap water in which 16.4 g (0.25 mol) of potassium hydroxide with a purity of 86% were dissolved.

After cooling of the reaction mixture, the reaction mixture was adjusted to pH 3 by using hydrochloric acid, so that crystals separated out. The resulting crystals were recrystallized from ethyl acetate, so that 20.5 g of 4-(β-phenoxyethoxy)phthalic acid were obtained. The melting point of this compound was 184° C.

The results of the NMR spectral analysis of the obtained product are shown in Table 6. The product was identified as 4-(β-phenoxyethoxy)phthalic acid through the NMR analysis.

TABLE 6

| 4.38 ppm | (a, b) | 4H |
|---|---|---|
| 6.07 ppm | (c) | 2H |
| 7.22 ppm | (d) | 5H |
| 7.76–7.90 ppm | (e) | 1H | structure: (d)(d)(d)(d)–OCH₂CH₃O–(c)(e)(c)–COOH, COOH
(with labels (a)(b) on the OCH₂CH₃O chain)

EXAMPLE 1

[Formation of thermosensitive recording layer]

A mixture of the following components was separately dispersed and pulverized in a ball mill using glass balls for 2 days, so that a Liquid A, a Liquid B and a Liquid C were prepared:

| | Parts by Weight |
|---|---|
| [Liquid A] | |
| 3-dibutylamino-6-methyl-7-anilinofluoran | 20 |
| 10% aqueous solution of polyvinyl alcohol | 20 |
| Water | 60 |
| [Liquid B] | |
| 4-benzyloxyphthalic acid (Compound No. I-1 in Table 1) | 20 |
| 10% aqueous solution of polyvinyl alcohol | 20 |
| Water | 60 |
| [Liquid C] | |
| Silicon dioxide | 20 |
| Water | 80 |

10 parts by weight of the Liquid A, 30 parts by weight of the Liquid B, 10 parts by weight of the Liquid C, and 10 parts by weight of a dispersion of zinc stearate with a concentration of 30% were mixed to prepare a thermosensitive recording layer coating liquid. The thus prepared thermosensitive recording layer coating liquid was coated on a sheet of commercially available high quality paper with a basis weight of 52 g/m², serving as a support, and then dried in such a fashion that the deposition amount of the dye component was 0.5 g/m² on a dry basis, whereby a thermosensitive recording layer was formed on the support. Furthermore, the surface of the thus prepared thermosensitive recording layer was subjected to calendering so as to have a surface smoothness of 500 to 600 sec in terms of Bekk's smoothness.

Thus, a thermosensitive recording material No. 1 according to the present invention was obtained.

EXAMPLES 2 to 12 AND COMPARATIVE EXAMPLES 1 AND 2

The procedure for preparation of the thermosensitive recording material No. 1 according to the present invention in Example 1 was repeated except that 4-benzyloxyphthalic acid serving as a color developer for use in the Liquid B in Example 1 was replaced by the respective compounds shown in Table 7.

Thus, thermosensitive recording materials Nos. 2 to 12 according to the present invention and comparative thermosensitive recording materials Nos. 1 and 2 were obtained.

EXAMPLE 13

[Formation of intermediate layer]

A mixture of the following components was stirred and dispersed, so that a coating liquid D for an intermediate layer was prepared:

|  | Parts by Weight |
| --- | --- |
| [Liquid D] | |
| Aqueous dispersion of minute void particles (copolymer resin comprising styrene and acryl as the main components) (solid content: 38 wt. %, average particle diameter; 0.7 μm, and voidage: 80%) | 30 |
| Styrene - butadiene copolymer latex (solid content: 47.5 wt. %) | 10 |
| Water | 60 |

The thus obtained intermediate layer coating liquid D was coated on a sheet of commercially available high quality paper with a basis weight of 52 g/m², serving as a support, and then dried so as to have a coating amount of 5 g/m² on a dry basis, whereby an intermediate layer was formed on the support.

[Formation of thermosensitive recording layer]

A mixture of the following components was separately dispersed and pulverized in a ball mill using glass balls for 2 days, so that a Liquid A, a Liquid B and a Liquid C were prepared:

|  | Parts by Weight |
| --- | --- |
| [Liquid A] | |
| 3-dibutylamino-6-methyl-7-anilinofluoran | 20 |
| 10% aqueous solution of polyvinyl alcohol | 20 |
| Water | 60 |
| [Liquid B] | |
| 4-benzyloxyphthalic acid (Compound No. I-1 in Table 1) | 20 |
| 10% aqueous solution of polyvinyl alcohol | 20 |
| Water | 60 |
| [Liquid C] | |
| Silicon dioxide | 20 |
| Water | 80 |

10 parts by weight of the Liquid A, 30 parts by weight of the Liquid B, 10 parts by weight of the Liquid C, and 10 parts by weight of a dispersion of zinc stearate with a concentration of 30% were mixed to prepare a thermosensitive recording layer coating liquid. The thus prepared thermosensitive recording layer coating liquid was coated on the above prepared intermediate layer and dried in such a fashion that the deposition amount of the dye component was 0.5 g/m² on a dry basis, whereby a thermosensitive recording layer was formed on the intermediate layer. Furthermore, the surface of the thus prepared thermosensitive recording layer was subjected to calendering so as to have a surface smoothness of 500 to 600 sec in terms of Bekk's smoothness, whereby a thermosensitive recording material No. 13 according to the present invention was obtained.

EXAMPLES 14 TO 18 AND COMPARATIVE EXAMPLES 3 AND 4

The procedure for preparation of the thermosensitive recording material No. 13 according to the present invention in Example 13 was repeated except that 4-benzyloxyphthalic acid serving as a color developer for use in the Liquid B in Example 13 was replaced by the respective compounds shown in Table 7.

Thus, thermosensitive recording materials Nos. 14 to 18 according to the present invention and comparative thermosensitive recording materials Nos. 3 and 4 were obtained.

EXAMPLE 19

[Formation of intermediate layer]

A mixture of the following components was stirred and dispersed, so that a coating liquid E for an intermediate layer was prepared:

|  | Parts by Weight |
| --- | --- |
| [Liquid E] | |
| Aqueous dispersion of minute void particles (copolymer resin comprising vinylidene chloride and acrylonitrile as the main components) (solid content: 32 wt. %, average particle diameter: 5 μm, and voidage: 92%) | 30 |
| Styrene - butadiene copolymer latex (solid content: 47.5 wt. %) | 10 |
| Water | 60 |

The thus obtained intermediate layer coating liquid E was coated on a sheet of commercially available high quality paper with a basis weight of 52 g/m², serving as a support, and then dried so as to have a coating amount of 5 g/m² on a dry basis, whereby an intermediate layer was formed on the support.

[Formation of thermosensitive recording layer]

A mixture of the following components was separately dispersed and pulverized in a ball mill using glass balls for 2 days, so that a Liquid A, a Liquid B and a Liquid C were prepared:

|  | Parts by Weight |
| --- | --- |
| [Liquid A] | |
| 3-dibutylamino-6-methyl-7-anilinofluoran | 20 |
| 10% aqueous solution of polyvinyl alcohol | 20 |

-continued

|  | Parts by Weight |
| --- | --- |
| Water | 60 |
| [Liquid B] | |
| 4-benzyloxyphthalic acid | 20 |
| (Compound No. I-1 in Table 1) | |
| 10% aqueous solution of polyvinyl alcohol | 20 |
| Water | 60 |
| [Liquid C] | |
| Silicon dioxide | 20 |
| Water | 80 |

10 parts by weight of the Liquid A, 30 parts by weight of the Liquid B, 10 parts by weight of the Liquid C, and 10 parts by weight of a dispersion of zinc stearate with a concentration of 30% were mixed to prepare a thermosensitive recording layer coating liquid. The thus prepared thermosensitive recording layer coating liquid was coated on the above prepared intermediate layer and dried in such a fashion that the deposition amount of the dye component was 0.5 g/m$^2$ on a dry basis, whereby a thermosensitive recording layer was formed on the intermediate layer. Furthermore, the surface of the thus prepared thermosensitive recording layer was subjected to calendering so as to have a surface smoothness of 500 to 600 sec in terms of Bekk's smoothness, whereby a thermosensitive recording material No. 19 according to the present invention was obtained.

EXAMPLES 20 TO 24 AND COMPARATIVE EXAMPLES 5 AND 6

The procedure for preparation of the thermosensitive recording material No. 19 according to the present invention in Example 19 was repeated except that 4-benzyloxyphthalic acid serving as a color developer for use in the Liquid B in Example 19 was replaced by the respective compounds shown in Table 7.

Thus, thermosensitive recording materials Nos. 20 to 24 according to the present invention and comparative thermosensitive recording materials Nos. 5 and 6 were obtained.

Using a commercially available test apparatus for evaluating the thermal coloring performance of thermo-sensitive sheets, made by Matsushita Electronic Components Co., Ltd., images were recorded on each of the thermosensitive recording materials obtained in Examples 1 to 24 and Comparative Examples 1 to 6 under the conditions that the applied electric power was 0.68 W/dot and the period for one line was 10 ms/line, with the pulse width changed to 0.4 msec and 0.6 msec. The coloring density of the recorded image and the density of the background were measured by Mcbeth densitometer RD-914.

TABLE 7

|  | Color Developer | Coloring Density | | Density of Background |
| --- | --- | --- | --- | --- |
|  |  | 0.4 ms | 0.6 ms |  |
| Ex. 1 | 4-benzyloxyphthalic acid [Compound No. I-1] | 0.45 | 0.89 | 0.12 |
| Ex. 2 | 4-benzyloxyisophthalic acid [Compound No. I-19] | 0.56 | 1.01 | 0.12 |
| Ex. 3 | 4-(4'-phenoxybutoxy)-phthalic acid [Compound No. I-29] | 0.63 | 1.31 | 0.11 |
| Ex. 4 | 4-(β-phenoxyethoxy)-phthalic acid [Compound No. I-3] | 0.55 | 1.26 | 0.11 |
| Ex. 5 | 5-benzyloxysulfonyl-isophthalic acid [Compound No. II-1] | 0.40 | 0.80 | 0.11 |
| Ex. 6 | 5-phenethylsulfonyl-isophthalic acid [Compound No. II-4] | 0.47 | 0.95 | 0.11 |
| Ex. 7 | 5-α-methylbenzyl-sulfonylisophthalic acid [Compound No. II-5] | 0.44 | 0.86 | 0.11 |
| Ex. 8 | 5-benzyloxycarbonyl-isophthalic acid [Compound No. III-1] | 0.40 | 0.81 | 0.12 |
| Ex. 9 | 5-phenethyloxy-carbonylisophthalic acid [Compound No. III-2] | 0.41 | 0.79 | 0.12 |
| Ex. 10 | 5-phenoxypropaneoxy-carbonylisophthalic acid [Compound No. III-29] | 0.40 | 0.80 | 0.12 |
| Ex. 11 | 4-(4'-phenoxy-butylthio)phthalic acid [Compound No. IV-3] | 0.43 | 0.83 | 0.11 |
| Ex. 12 | 4-(4'-phenoxy-butylthio)isophthalic acid [Compound No. IV-8] | 0.41 | 0.79 | 0.11 |
| Ex. 13 | 4-benzyloxyphthalic acid [Compound No. I-1] | 0.62 | 1.04 | 0.12 |
| Ex. 14 | 4-(4'-phenoxybutoxy)-phthalic acid [Compound No. I-29] | 0.84 | 1.31 | 0.11 |
| Ex. 15 | 4-(β-phenoxyethoxy)-phthalic acid [Compound No. I-3] | 0.80 | 1.31 | 0.11 |
| Ex. 16 | 5-benzyloxysulfonyl-isophthalic acid [Compound No. II-1] | 0.56 | 0.91 | 0.10 |
| Ex. 17 | 5-benzyloxycarbonyl-isophthalic acid [Compound No. III-1] | 0.54 | 0.90 | 0.12 |
| Ex. 19 | 4-(4'-phenoxy-butylthio)phthalic acid [Compound No. IV-3] | 0.59 | 0.96 | 0.11 |
| Ex. 19 | 4-benzyloxyphthalic acid [Compound No. I-1] | 0.76 | 1.22 | 0.12 |
| Ex. 20 | 4-(4'-phenoxybutoxy)-phthalic acid [Compound No. I-29] | 1.02 | 1.32 | 0.11 |
| Ex. 21 | 4-(β-phenoxyethoxy)-phthalic acid [Compound No. I-3] | 0.99 | 1.32 | 0.11 |
| Ex. 22 | 5-benzyloxysulfonyl-isophthalic acid [Compound No. II-1] | 0.72 | 1.07 | 0.10 |
| Ex. 23 | 5-benzyloxycarbonyl-isophthalic acid [Compound No. III-1] | 0.69 | 1.03 | 0.12 |
| Ex. 24 | 4-(4'-phenoxy-butylthio)phthalic acid [Compound No. IV-3] | 0.71 | 1.08 | 0.11 |

TABLE 7-continued

| | Color Developer | Coloring Density 0.4 ms | Coloring Density 0.6 ms | Density of Background |
|---|---|---|---|---|
| Comp. Ex. 1 | 4,4'-dihydroxy-3,3'-diallyl diphenyl sulfone | 0.42 | 0.86 | 0.11 |
| Comp. Ex. 2 | 4,4'-isopropylidene diphenol | 0.65 | 1.31 | 0.12 |
| Comp. Ex. 3 | 4,4'-dihydroxy-3,3'-diallyl diphenyl sulfone | 0.55 | 1.07 | 0.11 |
| Comp. Ex. 4 | 4,4'-isopropylidene diphenol | 0.86 | 1.34 | 0.12 |
| Comp. Ex. 5 | 4,4'-dihydroxy-3,3'-diallyl diphenyl sulfone | 0.80 | 1.22 | 0.11 |
| Comp. Ex. 6 | 4,4'-isopropylidene diphenol | 1.01 | 1.35 | 0.12 |

Furthermore, thermal recording was carried out on each thermosensitive recording material using a heated block of 150° C. under the application of a pressure of 2 kg/cm² thereto for one second. Each test sample obtained by the above-mentioned thermal recording was subjected to the following tests:

(1) Oil-resistance test; Cottonseed oil (a reagent made by Kanto Chemical Co., Inc.) was applied to the surface of each test sample. After the test sample was allowed to stand at 40° C. in a dry condition for 16 hours, the coloring density of the image and the density of the background were measured by Mc beth densitometer RD-914. (2) Plasticizer-resistance test: Three PVC films (made by Shin-Etsu Polymer Co., Ldt.) were laminated and such a laminated firm was placed on each test sample under the application of a load of 5 kg. After the test sample was allowed to stand in the above-mentioned state at 40° C. in a dry condition for 16 hours, the coloring density of the image and the density of the background were measured by Mcbeth densitometer RD-914.

The results are shown in Table 8.

TABLE 8

| | Before Tests | | After Oil-resistance Test | | After Plasticizer-resistance Test | |
|---|---|---|---|---|---|---|
| | Coloring Density | Density of Background | Coloring Density | Density of Background | Coloring Density | Density of Background |
| Ex. 1 | 1.36 | 0.12 | 1.27 | 0.16 | 1.24 | 0.12 |
| Ex. 2 | 1.34 | 0.12 | 1.03 | 0.17 | 1.01 | 0.14 |
| Ex. 3 | 1.34 | 0.11 | 1.33 | 0.13 | 1.29 | 0.12 |
| Ex. 4 | 1.33 | 0.11 | 1.33 | 0.14 | 1.30 | 0.13 |
| Ex. 5 | 1.34 | 0.10 | 1.37 | 0.18 | 1.19 | 0.15 |
| Ex. 6 | 1.36 | 0.11 | 1.40 | 0.18 | 1.21 | 0.16 |
| Ex. 7 | 1.30 | 0.12 | 1.23 | 0.15 | 1.22 | 0.15 |
| Ex. 8 | 1.40 | 0.12 | 1.36 | 0.18 | 1.22 | 0.16 |
| Ex. 9 | 1.30 | 0.12 | 1.03 | 0.17 | 1.05 | 0.17 |
| Ex. 10 | 1.35 | 0.11 | 1.04 | 0.16 | 1.06 | 0.17 |
| Ex. 11 | 1.28 | 0.11 | 1.35 | 0.16 | 1.20 | 0.12 |
| Ex. 12 | 1.36 | 0.10 | 1.30 | 0.14 | 1.08 | 0.12 |
| Ex. 13 | 1.36 | 0.12 | 1.25 | 0.16 | 1.22 | 0.12 |
| Ex. 14 | 1.34 | 0.11 | 1.34 | 0.13 | 1.28 | 0.12 |
| Ex. 15 | 1.35 | 0.11 | 1.34 | 0.15 | 1.29 | 0,13 |
| Ex. 16 | 1.35 | 0.10 | 1,35 | 0.17 | 1.17 | 0.15 |
| Ex. 17 | 1.41 | 0.13 | 1.36 | 0.18 | 1.21 | 0.16 |
| Ex. 18 | 1.39 | 0.11 | 1.37 | 0.15 | 1.22 | 0.12 |
| Ex. 19 | 1.37 | 0.12 | 1.25 | 0.15 | 1.21 | 0.13 |
| Ex. 20 | 1.36 | 0.11 | 1.33 | 0.13 | 1.27 | 0.12 |
| Ex. 21 | 1.36 | 0.12 | 1.35 | 0.14 | 1.29 | 0.12 |
| Ex. 22 | 1.35 | 0.10 | 1.36 | 0.18 | 1.14 | 0.14 |
| Ex. 23 | 1.40 | 0.12 | 1.35 | 0.17 | 1.21 | 0.18 |
| Ex. 24 | 1.39 | 0.11 | 1.38 | 0.15 | 1.23 | 0.12 |
| Comp. Ex. 1 | 1.36 | 0.11 | 0.53 | 0.19 | 0.28 | 0.18 |
| Comp. Ex. 2 | 1.33 | 0.11 | 0.30 | 0.16 | 0.22 | 0.17 |
| Comp. Ex. 3 | 1.37 | 0.12 | 0.49 | 0.18 | 0.27 | 0.19 |
| Comp. Ex. 4 | 1.35 | 0.12 | 0.28 | 0.16 | 0.20 | 0.17 |
| Comp. Ex. 5 | 1.38 | 0.12 | 0.49 | 0.18 | 0.25 | 0.17 |
| Comp. Ex. 6 | 1.35 | 0.12 | 0.26 | 0.16 | 0.22 | 0.17 |

As can be seen from the results shown in Table 7 and 8, the thermal coloring sensitivity and the coloring density of the obtained images are excellent in the thermosensitive recording materials according to the present invention. In addition, the images recorded on the thermosensitive recording materials of the present invention are resistant to fats and oils, and plasticizers, so that the preservation stability of recorded images is excellent. Therefore, the thermosensitive recording materials of the present invention are regarded as very useful in the practical use.

The reason for the above-mentioned advantages is that the thermosensitive recording layer of the thermosensitive recording material of the present invention comprises the color developer comprising at least one compound selected from the group consisting of the compounds represented by formulas (I) to (IV).

When the intermediate layer comprising the plastic void particles is interposed between the support and the thermosensitive recording layer in the present invention, the thermal energy supplied by the thermal head can efficiently be utilized, so that the thermosensitivity is further improved.

Furthermore, the compounds Nos. I-3 and I-29 shown in Table 1 are novel compounds, which show excellent properties as the color developers for use in the thermosensitive recording material of the present invention.

What is claimed is:
1. A thermosensitive recording material comprising a support and a thermosensitive recording layer formed on said support, comprising a leuco dye and a color developer capable of inducing color formation in said leuco dye upon application of heat thereto, said color developer comprising at least one compound selected from the group consisting of compounds represented by formulas (I) to (IV);

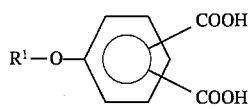
(I)

wherein R¹ is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group consisting of an alkyl group having 1 to 6 carbon atoms, an alkoxyl group having 1 to 6 carbon atoms, nitro group or a halogen,

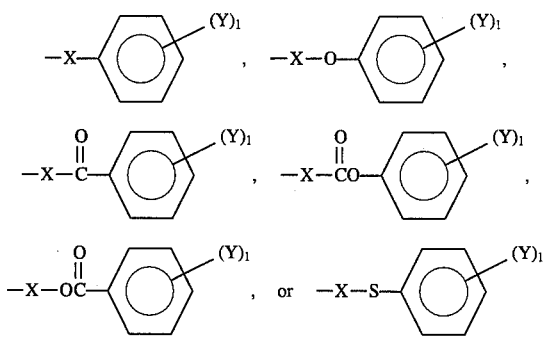

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and l is an integer of 0 to 5;

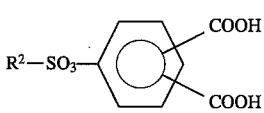
(II)

wherein R² is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group consisting of an alkyl group having 1 to 6 carbon atoms, an alkoxyl group having 1 to 6 carbon atoms, nitro group or a halogen,

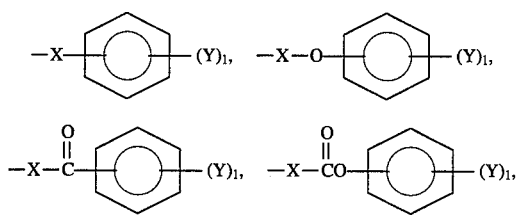

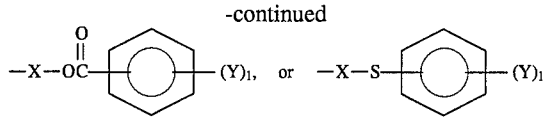

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and l is an integer of 0 to 5;

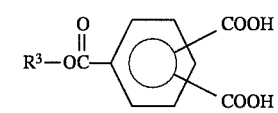
(III)

wherein R³ is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group consisting of an alkyl group having 1 to 6 carbon atoms, an alkoxyl group having 1 to 6 carbon atoms, nitro group or a halogen,

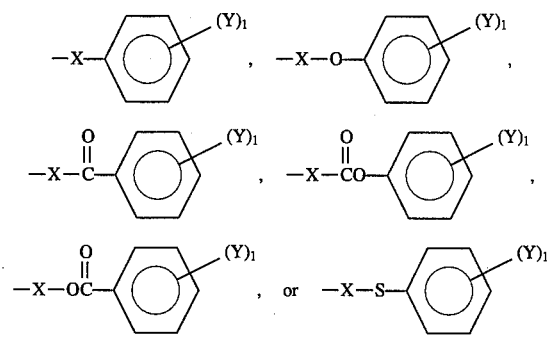

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and l is an integer of 0 to 5; and

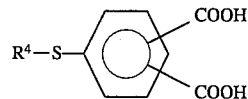
(IV)

wherein R⁴ is a saturated or unsaturated chain hydrocarbon group having 1 to 10 carbon atoms which may be branched, a chain hydrocarbon group having 1 to 10 carbon atoms which may be substituted by hydroxyl group or interrupted by an ether linkage or carbonyl group, an aryl group selected from the group consisting of phenyl group and naphthyl group, which may have a substituent selected from the group consisting of an alkyl group having 1 to 6 carbon atoms, an alkoxyl group having 1 to 6 carbon atoms, nitro group or a halogen,

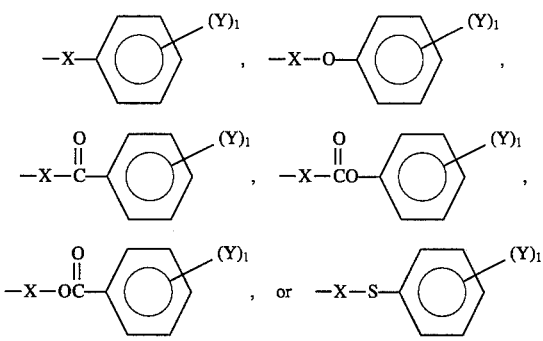

in which X is a saturated or unsaturated bivalent hydrocarbon group having 1 to 10 carbon atoms, or a bivalent hydrocarbon group having 1 to 10 carbon atoms which may be substituted by hydroxyl group or interrupted by an ether linkage or carbonyl group; and Y is an alkyl group having 1 to 6 carbon atoms, an alkoxyl group having 1 to 6 carbon atoms, nitro group or a halogen; and 1 is an integer of 0 to 5.

2. The thermosensitive recording material as claimed in claim 1, wherein said chain hydrocarbon group represented by $R^1$ to $R^4$ in formulas (I) to (IV) has 3 to 10 carbon atoms.

3. The thermosensitive recording material as claimed in claim 1, further comprising an intermediate layer which is provided between said support and said thermosensitive recording layer.

4. The thermosensitive recording material as claimed in claim 3, wherein said intermediate layer comprises plastic void particles comprising a thermoplastic resin.

5. The thermosensitive recording material as claimed in claim 4, wherein said void particles for use in said intermediate layer have an average particle diameter of 2 to 10 μm.

6. The thermosensitive recording material as claimed in claim 4, wherein said void particles for use in said intermediate layer have a voidage of 50% or more.

7. The thermosensitive recording material as claimed in claim 1, wherein said color developer for use in said thermosensitive recording layer comprises a phthalic acid derivative of formula (V):

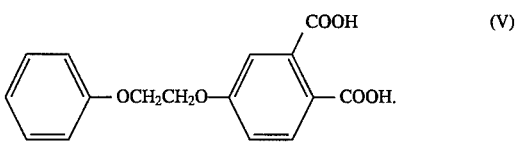

8. The thermosensitive recording material as claimed in claim 1, wherein said color developer for use in said thermosensitive recording layer comprises a phthalic acid derivative of formula (VI):

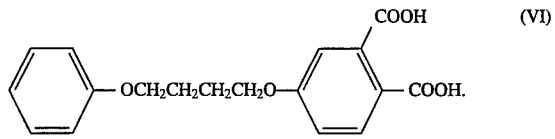

9. The thermosensitive recording material as claimed in claim 1, wherein said thermosensitive recording layer further comprises a filler selected from the group consisting of silica, aluminum hydroxide, kaolin and talc.

* * * * *

UNITED STATES PATENT AND TRADEMARK OFFICE
CERTIFICATE OF CORRECTION

PATENT NO. : 5,482,912
DATED : January 9, 1996
INVENTOR(S) : Hiromi FURUYA et al It is certified that error appears in the above-identified patent and that said Letters Patent is hereby corrected as shown below:

Column 27, line 54, after "RD-914." insert --The results are given in Table 7.--

Column 29, line 36, "Ldt." should read --Ltd.--.

Column 29, line 37, "firm" should read --film--.

Column 31, line 43, "  "

should read -- 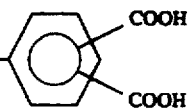 --.

Signed and Sealed this

Twenty-ninth Day of October 1996

*Attest:*

BRUCE LEHMAN

*Attesting Officer*   *Commissioner of Patents and Trademarks*